United States Patent [19]
Gairin et al.

[11] Patent Number: 6,087,441
[45] Date of Patent: Jul. 11, 2000

[54] STRUCTURALLY MODIFIED PEPTIDES THAT ARE RESISTANT TO PEPTIDASE DEGRADATION

[75] Inventors: Jean Edouard Gairin; Maha Ayyoub, both of Toulouse, France; Benoît Van Den Eynde, Brussels, Belgium; Honoré Mazarguil; Bernard Monsarrat, both of Toulouse, France

[73] Assignee: Ludwig Institute for Cancer Research, New York, N.Y.

[21] Appl. No.: 08/795,733

[22] Filed: Feb. 5, 1997

[51] Int. Cl.$^7$ .................. A61K 38/04; A61K 39/395; C07K 7/06; C07K 16/00
[52] U.S. Cl. .................. 525/54.11; 530/327; 530/328; 514/15; 514/16
[58] Field of Search .................. 530/327, 328; 525/54.1, 54.11; 514/15, 16

[56] References Cited

U.S. PATENT DOCUMENTS

| | | |
|---|---|---|
| 5,342,774 | 8/1994 | Boon et al. . |
| 5,554,506 | 9/1996 | van der Bruggen et al. . |
| 5,554,724 | 9/1996 | Melief et al. . |

FOREIGN PATENT DOCUMENTS 9403205  2/1994  WIPO .

OTHER PUBLICATIONS

Min Ding et al., "Cloning and Analysis of MAGE–1–Related Genes," *Biochemical and Biophysical Research Communications*, vol. 22:1:549–555 (1994).

Pierre van der Bruggen et al., "A peptide encoded by human gene MAGE–3 and presented by HLA–A2 induces cytolytic T lymphocytes that recognize tumor cells expressing MAGE–3," *Eur. J. Immunol.*, vol. 24:3038–3043 (1994).

C. De Smet et al., "Sequence and expression pattern of the human MAGE2 gene," *Immunogenetics*, vol. 39:121–129 (1994).

Jörg Ruppert et al., "Prominent Role of Secondary Anchor Residues in Peptide Binding to HLA–A2.1 Molecules," *Cell*, vol. 74:929–937 (1993).

Victor H. Engelhard, "Structure of Peptides Associated With Class I and Class II MHC Molecules," *Annu. Rev. Immunol.*, vol. 12:181–207 (1994).

Pierre G. Coulie et al., "A New Gene Coding for a Differentiation Antigen Recognized by Autologous Cytolytic T Lymphocytes on HLA–A2 Melanomas," *J. Exp. Med.*, vol. 180:35–42 (1994).

Esteban Celis et al., "Induction of anti–tumor cytotoxic T lymphocytes in normal human using primary cultures and synthetic peptide epitopes," *Proc. Natl. Acad. Sci. USA*, vol. 91:2105–2109 (1994).

A. R. M. Townsend et al., "The Epitopes of Influenza Nucleoproteiin Recognized by Cytotoxic T Lymphocytes Can Be Defined with Short Synthetic Peptides," *Cell*, vol. 44:959–968 (1968).

P. J. Bjorkman et al., "The foreign antigen binding site and T cell recognition regions of class I histocompatibility antigens," *Nature*, vol. 329:512–518 (1987).

M. Hubank et al., "Identifying differences in mRNA expression by representational difference analysis of cDNA," *Nucleic Acids Research*, vol. 22:25:5640–5648 (1994).

Etienne De Plaen et al., "Structure, chromosomal localization, and expression of 12 genes of the MAGE family," *Immunogenetics*, vol. 40:360–369 (1994).

Gordon Ada, "Twenty Years Into the Saga of MHC–Restriction" –*Immunology and Cell Biology*, vol. 72:447–454, (1994).

Peter Cresswell, "Questions of Presentations," *Nature*, vol. 343:–595–594, (1990).

P. Van Der Bruggen, et al. "A Gene Encoding An Antigen Recognized–By Cytolytic T Lymphocytes On A Human Melanoma" *Science*, vol. 254:1643–1647 (1991).

B. Van den Eynde, et al. "Human Tumour Antigens Recognized By–T–Cells: Perspectives For New Cancer Vaccines," *Antigen Processing and Presentation*, vol. 23 (1995).

*Primary Examiner*—Nathan M. Nutter
*Attorney, Agent, or Firm*—Fulbright & Jaworski

[57] ABSTRACT

Human melanoma cells bear antigens that are recognized by autologous CD8+ cytotoxic T-lymphocytes. The invention involves the reception of particular peptides analogues of the MZ2-E antigen by HLA molecules. Disclosed herein are peptide analogues of the tumor antigen MZ2-E that have been modified to resist peptidase degradation, and which bind HLA molecules to form a complex whose recognition by specific cytolytic T cells leads to lysis of the complex. The identification by cytolytic T cells of the peptide analogue/HLA complex may be used in diagnostics, or therapeutically.

23 Claims, 7 Drawing Sheets

| m/z | deduced sequence |
|-----|------------------|
| 976 | EADPTGHSY |
| 269 | SY |
| 526 | DPTGH |
| 726 | EADPTGH |
| 776 | DPTGHSY |
| 847 | ADPTGHSY |

FIG. 3L [Aib², NMeS⁸] MZ2-E

FIG. 3K [NMeS⁸] MZ2-E

FIG. 3J [Aib²] MZ2-E

FIG. 3I MZ2-E

FIG. 3P [Aib², NMeS⁸] MZ2-E

FIG. 3O [NMeS⁸] MZ2-E

FIG. 3N [Aib²] MZ2-E

FIG. 5B
[Aib$^2$, NMe-Ser$^8$]-MZ2–E

FIG. 5C
[Aib$^2$,D-His$^7$]-MZ2–E

FIG. 5D
[NMe-Ala$^2$, NMe-Ser$^8$]-MZ2–E

STRUCTURALLY MODIFIED PEPTIDES THAT ARE RESISTANT TO PEPTIDASE DEGRADATION

FIELD OF THE INVENTION

This invention relates to the field of immunology. In particular, it relates to peptides which form complexes with HLA molecules, and exhibit a half-life of more than 30 minutes relative to degradation by peptidase. More particularly, the present invention contemplates a class of peptides of a particular nonapeptide, MZ2-E, which have been modified to resist peptidase degradation. The contemplated peptides are useful in many ways, e.g., as immunogens and as materials which target and bind MHC/HLA molecules.

BACKGROUND AND PRIOR ART

The study of the recognition or lack of recognition of foreign antigen by a host organism has proceeded in many different directions. Understanding of the field presumes some understanding of both basic immunology, and protein chemistry.

The immune system is constantly at war, fighting viruses, bacteria, and other pathogens that try to invade the body. In this war, it uses a diverse range of effectors in order to deal with the threat to health posed by an equally diverse range of infectious organisms that are prevalent in the environment. For example, T-lymphocytes play a central role in the induction and regulation of the immune response and in the execution of immunological functions. These cells are particularly important in tumor rejection and in fighting viral infections.

However, antigen recognition by the T-lymphocytes is restricted by cell-surface glycoproteins encoded by the highly polymorphic genes of the major histocompatibility complex (MHC) molecules. This discrimination requires a T cell specific for a particular combination of an HLA molecule and a peptide rather than the intact foreign antigen itself. If a specific T cell is not present, there is no T cell response even if its partner complex is present. Similarly, there is no response if the specific complex is absent, but the T cell is present. Much work has focused on the mechanisms by which proteins are processed into the HLA binding peptide. See, in this regard, Cresswell, Nature 343: 593–594 (1990); Aichinger, et al. Biochemical Society Trans, 23: 657–659, (1995); Fremont et al., Science 257: 919 (1992); and Lanzavecchia, Science 260:937–943 (1993); Matsumura et al., Science 257: 927 (1992); Latron et al., Science 257: 964 (1992).

MHC class I molecules are expressed by almost all nucleated cells of the body and, in the main, present peptides derived from intracellular proteins to cytotoxic T cells expressing the CD8 co-receptor. Activation of the cytotoxic T cell, in turn, results in the destruction of the target cells by apoptosis induced by perforin/granzyme and/or Fas ligand.

In the case of MHC class I molecules, the peptide fragments usually contain from 8 to 11 amino acids and are generated inside the antigen presenting cells by a complex machinery involving proteases, peptide transporters and molecular chaperones. See Roitt, et al. *Immunology* (Mosby-Year Book Europe, 1993).

Although intact proteins need to be processed to generate antigenic peptide, soluble peptides are also known to directly bind to small fractions of empty MHC class I or II molecules present on cell surfaces. See in this regard, Braciale & Braciale, Immunology Today, 12(4): 124–129 (1991); Elliot, Immunology Today 12(11): 386–388 (1991).

MHC class II molecules are expressed on a more limited set of antigen presenting cells, exemplified by B-cells, T-cells themselves, macrophages, and dendritic cells. These molecules present peptides in a way which is similar to class I molecules, except that the peptide is generally derived from an exogenous protein from the intercellular environment (e.g., bacteria). Class II molecules present their captured peptide to helper T cells expressing the CD4 co-receptor molecule and their activation generally results in the secretion of cytokines.

Thus, specific T cell immunity is controlled by two selective and independent binding events: first, binding of the peptide fragments of the antigens by the MHC class molecules, and second, binding of the resulting complexes by the clonotypic antigen receptors of the T cell. See, in this regard, Ada, Immunology and Cell Biology 72:447–454 (1994).

Tumor antigens are characteristic of tumor tissue and thus may be considered tissue specific. Tumor antigens result from alterations that frequently occur in malignant transformation of normal tissue. The alteration may be quantitative in that a particular normal antigen may decrease or increase in concentration. Such normal antigens that have increased concentration in tumors are generally referred to as "Tumor Associated Antigens (TAAs)" Antigenic alteration may also be qualitative in that a new antigen, foreign to the host, may appear. These are termed "Tumor-Specific Antigens (TSAs")" and may be present as new cell-surface structures or as new intracellular structures in the cytoplasm or nucleus.

Tumor specific antigens were first clearly demonstrated in mice that had been immunized with cells from a methylcholanthrene-induced sarcoma taken from syngeneic mice. These molecules were "recognized" by T cells in the recipient animal, and provoked a cytolytic T cell ("CTL" hereafter) response with lysis of the transplanted cells. The antigens expressed by the tumors and which elicited the T cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "Tumor Specific Transplantation Antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974) Prehn, R. T., and Main, J. M, Journal of Natl. Cancer Inst. 18:769 (1974).

While T cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum+" cells). When these tum+ cells are mutagenized, they are rejected by syngeneic mice, and fail to form tumors (thus "tum−"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum− variants fail to form progressive tumors because they elicit an immune rejection process. The evidence in favor of this hypothesis includes the ability of "tum−" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected tum− cells of mastocytoma P815 multiply exponentially for 12–15 days, and then are eliminated in only a few days in the midst of an influx of lymphocytes and macrophage (Uyttenhove et al., J. Exp. Med. 152: 1175–1183 (1980)). Further evidence includes the observation that mice acquire an immune memory which permits them to resist subsequent challenge to the same tum− variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "TRA" in a tumor which is a target for a syngeneic rejection response. Similar results have been obtained when foreign genes have been transfected into spontaneous tumors. See Fearson et al., Cancer Res. 48: 2975–1980 (1988) in this regard.

The extent to which these antigens have been studied, has been via cytolytic T cell characterization studies, in vitro i.e., the study of the identification of the antigen by a particular cytolytic T cells ("CTL" hereafter) subset. The subset proliferates upon recognition of the presented tumor rejection antigen, and the cells presenting the antigen are lysed.

Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987).

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum− variants following mutagenesis, including variants referred to as P91A (DePlaen, supra), 35B (Szikora, supra), and P198 (Sibille, supra).

Hence, with reference to the literature, a cell line can be tum+, such as the line referred to as "P1", and can be provoked to produce tum−variants. Since the tum− phenotype differs from that of the parent cell line, one expects a difference in the DNA of tum− cell lines as compared to their tum+ parental lines, and this difference can be exploited to locate the gene of interest in tum− cells. As a result, it was found that genes of tum− variants such as P91A, 35B and P198 differ from their normal alleles by point mutations in the coding regions of the gene. See Szikora and Sibille, supra, and Lurquin et al., Cell 58: 293–303 (1989). This has proved not to be the case with the "Tumor Rejection Antigens TRAs" of this invention. These papers also demonstrated that peptide derived from the tum− antigen are presented by the H-2 molecule for recognition by CTLs. P91A is presented by $L^d$, P35 by $D^d$ and P198 by $K^d$.

Human melanoma cells also bear antigens that are recognized by autologous CD8+ cytolytic T cells, which can be derived from blood lymphocytes or from tumor-infiltrating lymphocytes. In PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific cytolytic T lymphocytes. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. Pat. No. 5,342,774, incorporated by reference in its entirety, which discloses the "MAGE" family of tumor rejection antigen precursors.

The tum− antigens are only present after the tumor cells are mutagenized. In contrast, tumor rejection antigens—and this is a key distinction—are present on cells of a given tumor without mutagenesis.

U.S. Pat. No. 5,405,940, the disclosure of which is incorporated by reference, contemplates isolated nonapeptides derived from MAGE genes. In this patent, it is explained that the MAGE-1 gene codes for a TRAP which is processed to nonapeptides that are presented by HLA-A1 molecules. According to this patent, the nonapeptides are derived from expression products of the MAGE gene family. The resulting complexes are identified by cytolytic T cells, which can be used in diagnostics or therapeutically. The nonapeptides which bind to HLA-A1 follow a "rule" for binding in that a motif is satisfied. In this regard, see e.g. PCT/US93/07421; Falk et al., Nature 351: 290–296 (1991); Engelhard, Ann Rev. Immunol. 12: 181–207 (1994); Ruppert et al., Cell 74: 929–937 (1993); Rötzschke et al., Nature 348: 252–254 (1990); Bjorkman et al., Nature 329: 512–518 (1987); Traversari et al., J. Exp. Med. 176: 1453–1457 (1992). These references teach that given the known specificity of particular peptide for particular HLA molecules, one should expect a particular peptide to bind to at least one HLA molecule.

A cursory review of the development of the field may be found in Barinaga, "Getting Some 'Backbone': How MHC Binds Peptide", Science 257: 880 (1992); also, see Fremont et al., Science 257: 919 (1992); Matsumura et al., Science 257: 927 (1992); Latron et al., Science 257: 964 (1992). These papers generally point to a preference that the peptide which binds to an MHC/HLA molecule be nine amino acids long (a "nonapeptide"), and to the importance of two so-called anchor residues (most commonly the second and ninth residues of the nonapeptide).

Studies on the MAGE family of genes have now revealed that particular peptides are in fact presented on the surface of tumor cells, and that the presentation of the peptide requires that the presenting molecule be a specific HLA molecule. Complexes of the MAGE-1 tumor rejection antigen (the "TRA" or nonapeptide") and the HLA leads to lysis of the cell presenting it by CTL. This observation has both diagnostic and therapeutic implications, as discussed herein.

It has also been found that, when comparing homologous regions of various MAGE genes to the region of the MAGE-1 gene coding for the relevant nonapeptide, there is a great deal of homology. Homologous peptides can be used for various purposes which includes their use as immunogens, either alone or coupled to carrier peptide. The peptides are of sufficient size to constitute an antigenic epitope, and the antibodies generated thereto may then be used to identify the peptide, either as it exists alone, or as part of a larger polypeptide.

The nonapeptides may also be used as agents to identify various HLA subtypes on the surface of tumor cells, such as melanomas. Via this ability they may serve either as diagnostic markers, or as therapeutic agents. These features are discussed infra.

A second class of antigens represents differentiation antigens encoded by genes that are expressed in melanoma and in normal melanoctytes. Antigens derived from tyrosinase are exemplary of this class.

It is noteworthy that while the prior art peptides might arguably find use as therapeutics or in diagnostics, their contemplated use is short lived in view of their rapid degradation by peptidase activity.

OBJECTS AND SUMMARY OF THE INVENTION

It is an object of the present invention to provide isolated peptides having from 8–11 amino acids which are characterized as binding to an HLA molecule and having a half-life greater than 30 minutes, relative to degradation by peptidase.

It is an object of the present invention to provide peptides based on the MZ2-E antigen (see infra) which target and complex with HLA molecules. Recognition of the peptide analogue/HLA complex by cytolytic T lymphocytes, leads to lysis of the cells presenting the complex. This recognition may be used in diagnostics, or therapeutically.

The above object is achieved by structurally modified analogues of the tumor antigen MZ2-E.

A still further object of the present invention contemplates a method for treating a subject with a pathological condition which includes administering to the subject an amount of the peptide according to the invention, sufficient to alleviate the pathological condition. The administration of the peptide to the subject alleviates the pathological condition by provoking an effector cytolytic T cell response against the pathological condition.

A still further object of the invention contemplates a method for provoking proliferation of a CTL, comprising contacting a cell which presents a complex of the peptide analogues of the invention and an HLA molecule on its surface to a CTL, under conditions favoring proliferation thereof.

An alternative embodiment of the present invention relates to antibodies against the peptide analogues of the present invention.

Another embodiment of the present invention is directed to vaccines useful for treating a pathological disorder characterized by presentation on surfaces of pathological cell of HLA/peptide complexes of a type that differ from normal, wherein the vaccine includes the peptide analogues of the present invention together with a pharmaceutically acceptable adjuvant, which, when administered to a subject, provokes an immune response in the subject.

An alternative embodiment contemplates a method for determining presence of a substance in a sample which binds to a complex of an MHC molecule and a peptide, comprising contacting the sample with (i) a cell which presents said MHC molecule, and (ii) a peptide which consists of an amino acid sequence which specifically complexes with the MHC molecule, wherein the peptide has been modified to render it stable to peptidase degradation for at least 30 minutes, and (iii) determining interaction between said complex and said substance as a determination of the substance in said sample.

A still further embodiernt emraces an immunogenic composition comprising the peptide of claim 1, and a pharmaceutically acceptable adjuvant.

The above, and other objects, features and advantages of the present invention will become apparent from the following description read in conjunction with the accompanying drawings, in which like reference numerals designate the same elements.

DETAILED DESCRIPTION OF PREFERRED EMBODIMENTS

Tumor antigen MZ2-E is defined by the formula

Glu-Ala-Asp-Pro-Thr-Gly-His-Ser-Tyr. (SEQ. ID. NO: 1).

It is encoded by the MAGE-1 gene and expressed in 40% of human melanoma. It is presented at the cell surface by HLA-A1 and recognized in vitro by autologous CD8+ cytotoxic T lymphocytes. Thus, tumor antigen MZ2-E is a potential target for T cell based immunotherapy and can be used successfully for efficient in vitro or in vivo stimulation of antigen-specific CTL. As well, this antigen represents a promising approach for the development of peptide-based vaccine or anti-melanoma immunotherapy based on MZ2-E-specific T cell stimulation. However, the presentation of the MZ2-E antigen/nonamer by the HLA-A1 cells is limited by the degradation of the MZ2-E antigen by peptidase, which severely limits its therapeutic use.

Figure 1:
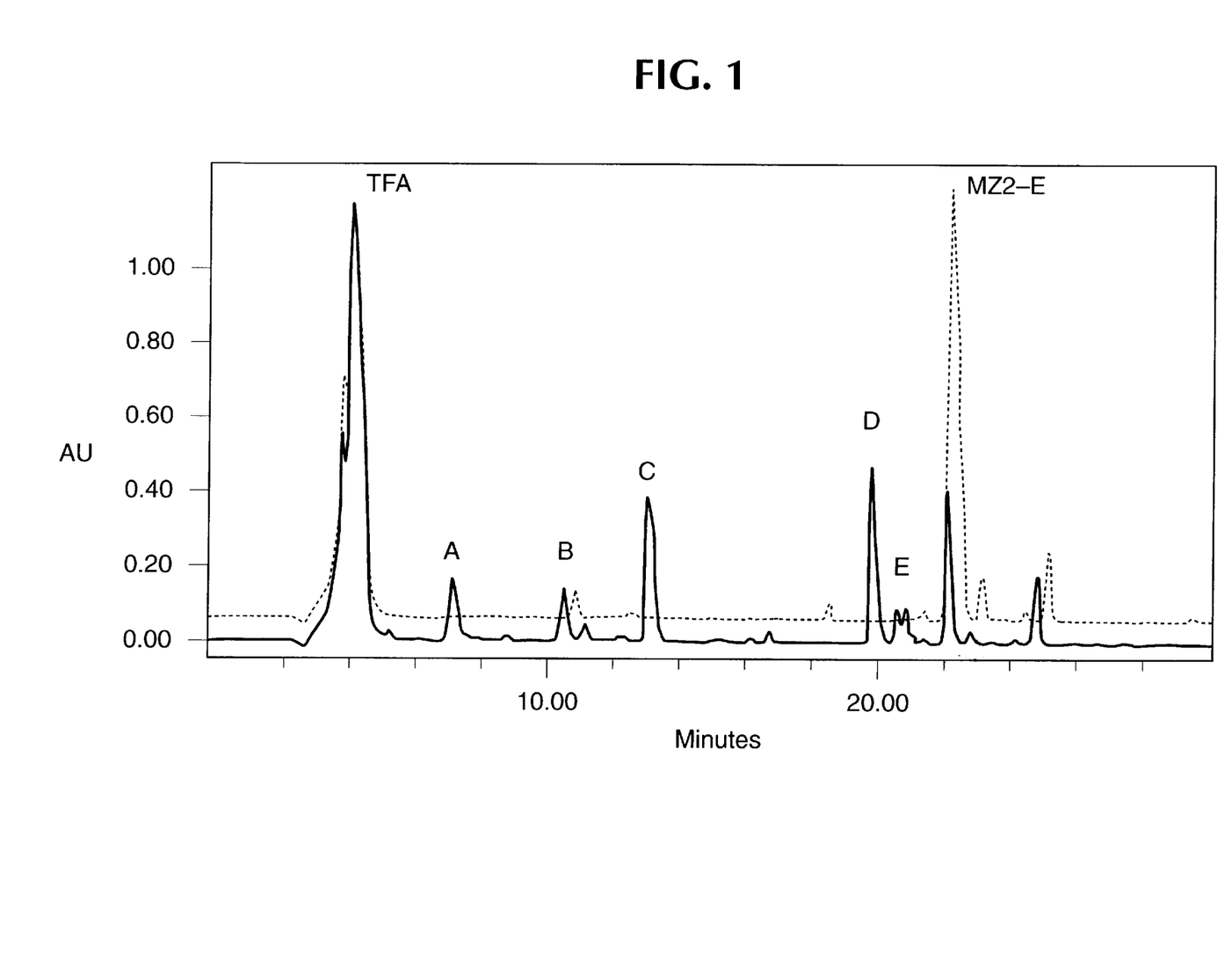
FIG. 1 describes the HPLC profile of a synthetic peptide corresponding to the MZ2-E antigen over a period of time after incubation with human serum containing peptidase. The various degradation products resulting from incubation with human serum are also shown.
Figure 2A:
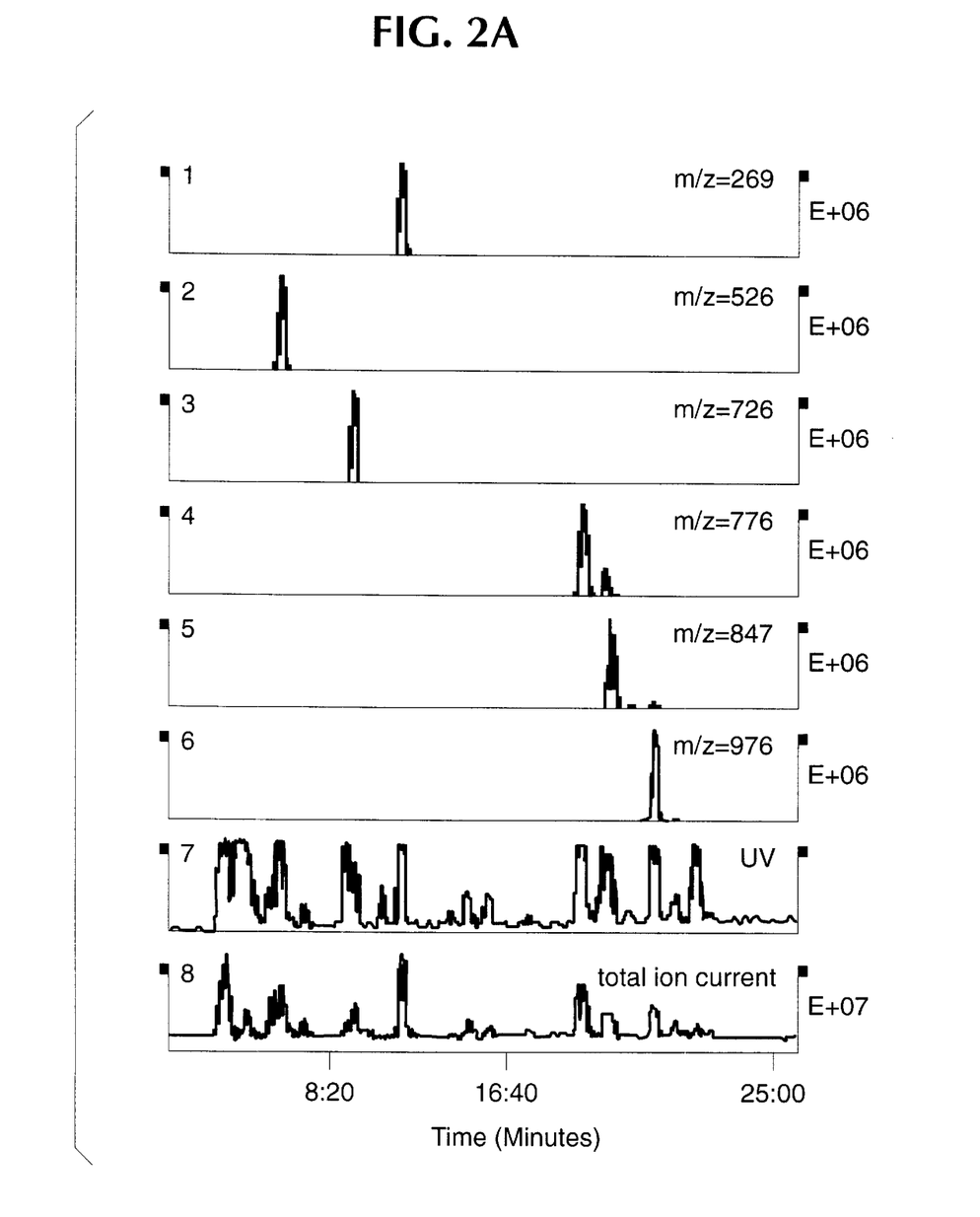
FIG. 2 shows, collectively, the amino acid sequence analysis of synthetic peptide analogues to the MZ2-E antigen as well as the amino acid sequence of its degradation products obtained by on-line RP-HPLC/ESI-MS or MS/MS mass spectrometry analysis.
Figure 2B:
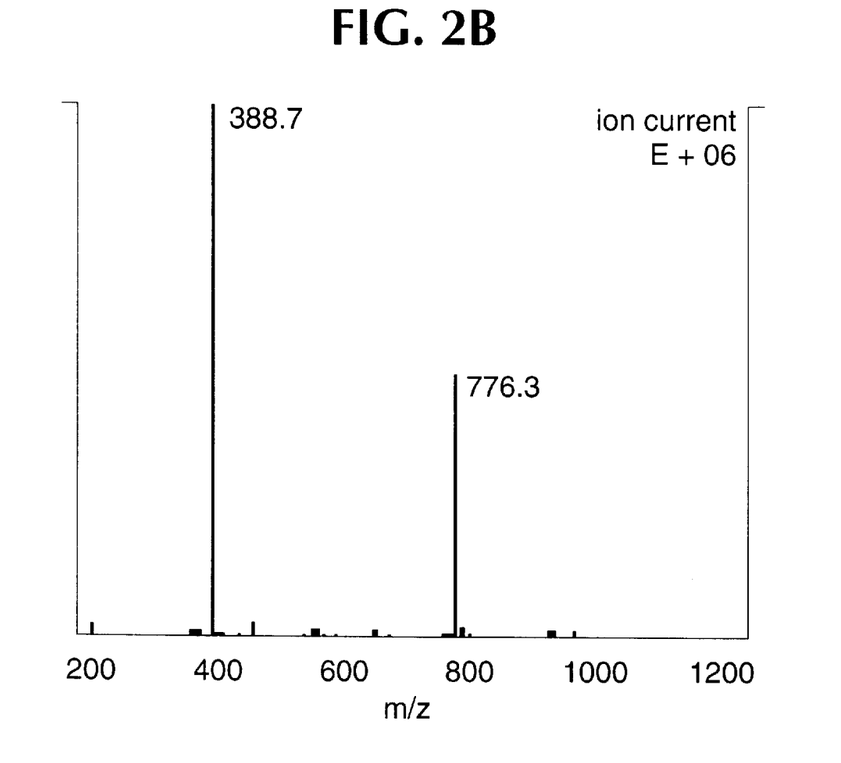
Figure 2C:
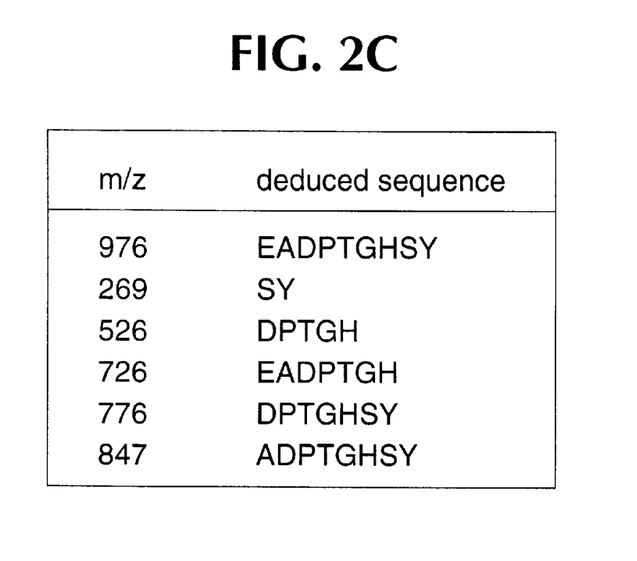
Figure 3A:
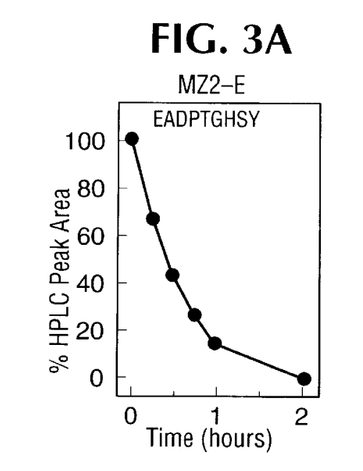
FIG. 3 shows the degradation kinetics of the synthetic peptide as well as its various analogues which were separated by RP-HPLC.
Figures 3B, 3C:
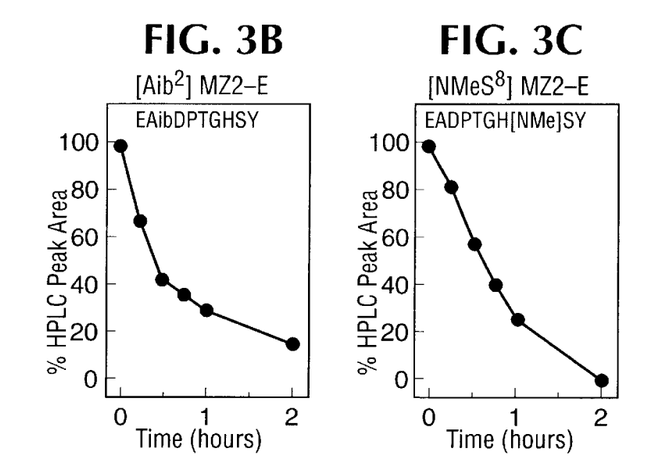
Figure 3D:
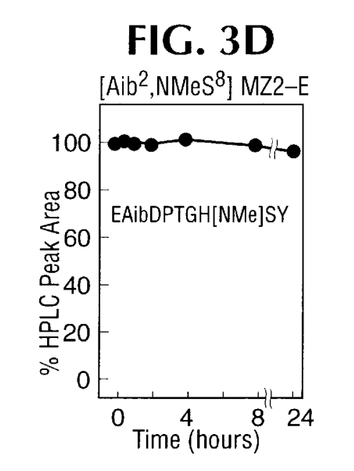
Figure 3E:
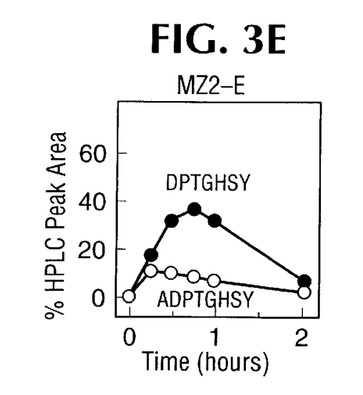
Figures 3F, 3G:
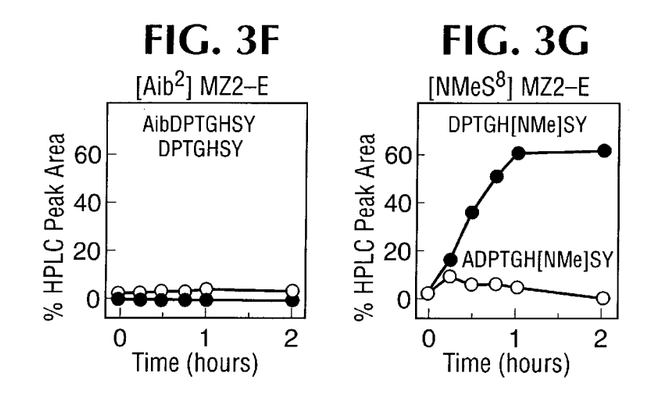
Figure 3H:
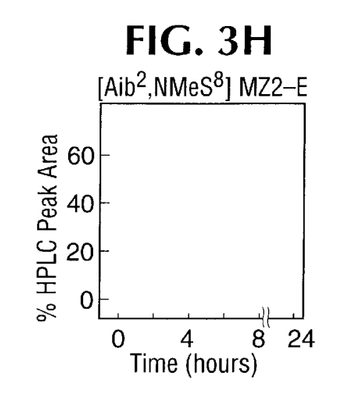
Figure 3I:
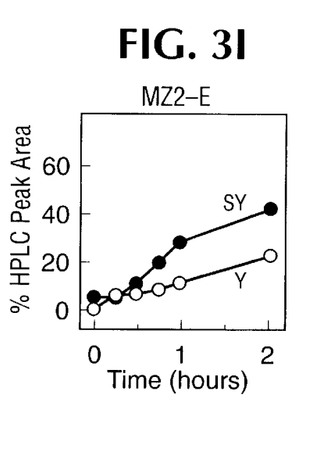
Figure 3J:
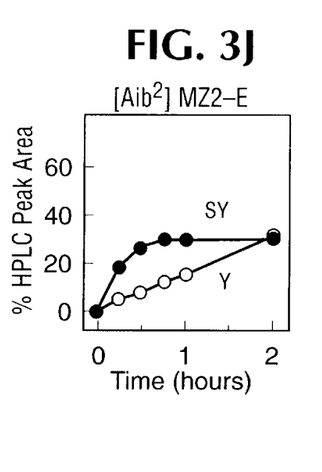
Figure 3K:
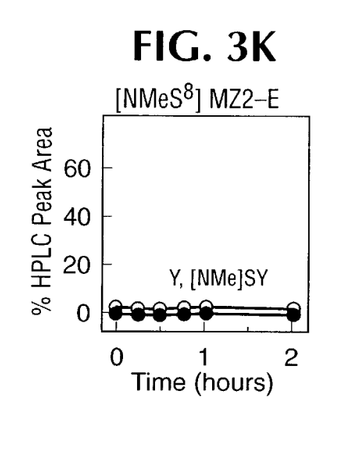
Figure 3L:
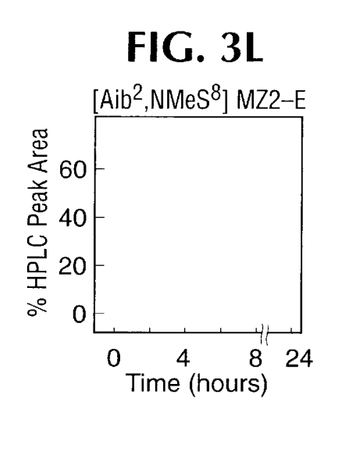
Figure 3M:
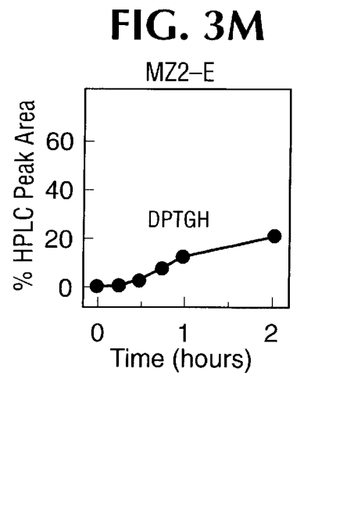
Figure 3N:
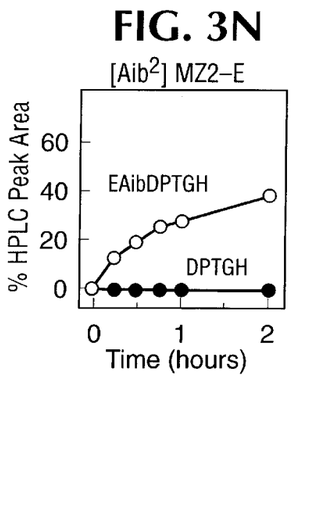
Figure 3O:
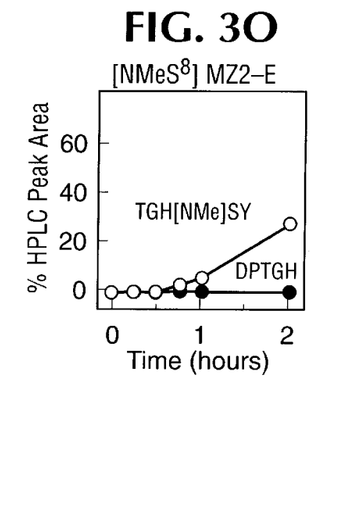
Figure 3P:
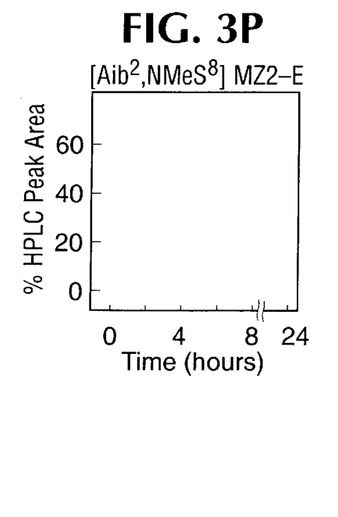
Figure 4:
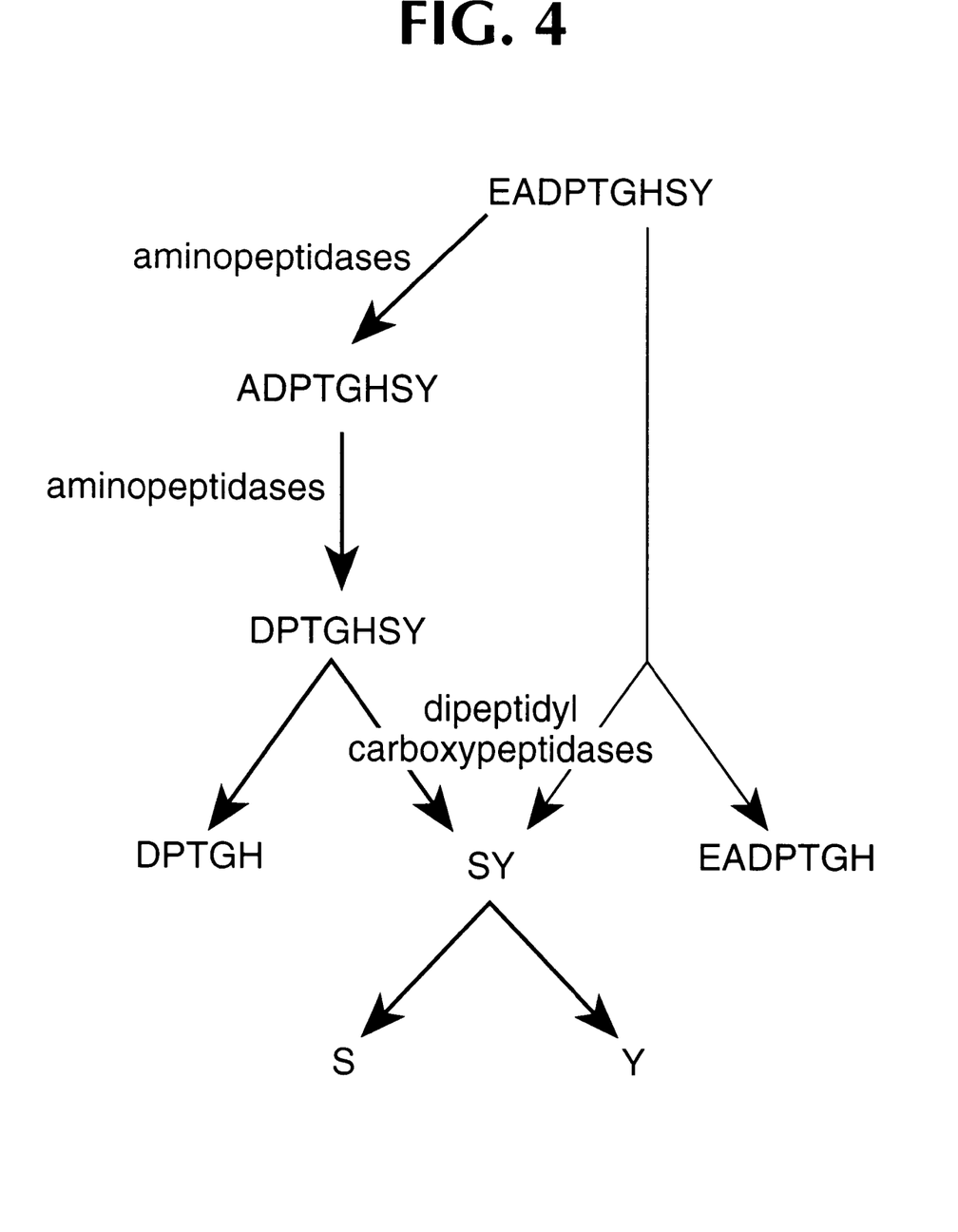
FIG. 4 shows a schematic of the proposed degradation pathway of the MZ2-E antigen by the actions of an amino peptidase and a dipeptidyl carboxy peptidase.

The present invention aims to remedy the deficiency attending the MZ2-E antigen by proposing structurally modified peptide analogues of the MZ2-E antigen that are characterized as (1) exhibiting a longer half-life than the parent MZ2-E antigen relative to peptidase degradation, and (2) binding the HLA molecule for presentation to CTLs specific for the complex. The peptides analogues exhibit a half-life of more than at least 30 minutes relative to degradation by peptidase, preferably more than 3.5 hours and more preferably more than 8 hours.

Briefly, the first step in developing the analogues of the MZ2-E antigen entailed finely analyzing the molecular mechanism of degradation of a synthetic peptide corresponding to the MZ2-E antigen in human serum. The second step encompassed synthesizing structurally modified analogues based on the knowledge that the degradation of the MZ2-E antigen involves two particular peptidases (1) an amino peptidase, and (2) a dipeptidyl carboxy peptidase. Thereafter, the peptide analogues were tested for their ability to resist peptidase degradation together with their affinity for binding HLA-A1 and their ability to sensitize target cells to lysis by MZ2-E specific cytotoxic T lymphocytes. These results were then compared to those obtained for the parent MZ2-E antigen. These steps are elaborated in detail below.

EXAMPLE I

A synthetic peptide corresponding to the MZ2-E antigen was synthesized by the solid-phase method on an Applied Biosystems 430A automated peptide synthesizer using the FMOC chemistry. The peptide was purified by high-pressure liquid chromatography on reverse-phase columns (RP300-C8 Brownlee Lab and an A.B.I. 130 apparatus). The purity of the synthetic peptide was determined to be greater than 98%.

The purified peptide was identified and confirmed by fast atom bombardment mass spectrum analysis. Peptide stock solutions were made at a peptide concentration of $3\times10^{-3}$ M in 5% dimethyl sulfoxide, 1% bovine serum albumin phosphate buffer saline (BSA-PBS) and stored at −20ÿ(77 EC.

EXAMPLE II

The synthetic peptide obtained in example 1 was incubated with human serum preheated for 15 minutes at 37 EC in the absence and in the presence of different peptidase inhibitors. At different times, an aliquot measuring about 150 $\mu$l was removed and the enzymatic reaction stopped by addition of 15 $\mu$l trifluoroacetic acid (TFA). Precipitated serum proteins were pelleted by centrifugation at 15000 rpm for 10 min at 4 EC. The supernatants were frozen and preserved at −20 EC until analysis.

During the above experiments, the following controls were realized (1) Peptide recovery after acidic precipitation was determined and titrated by HPLC analysis of a peptide solution ($10^{-3}$M) with or without 10% TFA.

(2) Peptide stability in a 10% TFA solution was also checked. Under these conditions, MZ2-E and its substituted analogues were found to be stable and did not precipitate in the presence of 10% TFA.

(3) The HPLC profile of a sample of serum alone precipitated by TFA was recorded to detect peaks corresponding to non-precipitated peptide present in the serum.

The peptide and its degradation product(s) were then separated by reverse phase chromatography (RP-HPLC). Peaks corresponding to the different products were quantified. HPLC analysis of the various peptide samples collected at different incubation times was conducted. As well, peptide degradation kinetics including the half-life of the various peptide samples was recorded together with any increase in the degradation products of the peptide samples under investigation.

The following HPLC conditions were used:

i) column: 5 $\mu$m×4.6 mm×25 cm, $C_{18}$, ii) gradient: 4–20% $CH_3CN$ (0.08% TFA in $H_2O$, 0.08% TFA in $CH_3CN$), 0–30 min, iii) UV detection: 200–300 nm using a Waters 996 photodiode array detector, iv) chromatograms obtained at 225 and 280 nm were also derived.

The mass and the amino acid sequence of the various degradation products were determined by on-line HPLC/mass spectrometry (MS) with electrospray ionization (ESI). The results are reported in FIG. 2.

Chromatographic conditions were the same as above except for the gradient (4–15% instead of 4–20%). MS analysis was performed with a TSQ-700 Finnigan Mat mass spectrometer. The entire HPLC flow was introduced into the ESI source through a capillary heated to 250 EC. Nitrogen was used as a nebulizing gas (sheath gas flow 80 psi, auxiliary gas 20 psi). The needle voltage was maintained at 5 kV. MS data (positive ions) were collected in the full scale mode (m/z 150–1200) at 2 ms per step.

It was observed that the synthetic peptide corresponding to the MZ2-E antigen rapidly degraded at 37 EC at $t_{1/2}$=½ h, by peptidase present in human serum in the absence of peptidase inhibitors. See FIGS. 1 and 3 (panel A). Thus, the parent MZ2-E antigen appears to have a half-life of about 30 minutes relative to degradation by peptidase.

On-line RP-HPLC/ESI-MS or MS/MS mass spectrometry analysis (exemplified in FIG. 2) revealed that two peptide bonds within the above MZ2-E nonapeptide were especially sensitive to peptidase degradation. These peptide bonds were determined to be as follows: $Glu^1$-$Ala^2$ and $His^7$-$Ser^8$.

Armed with this observation, it was hypothesized that the MZ2-E antigen was degraded by the actions of two types of peptidase: (1) an amino peptidase and (2) a dipeptidyl carboxy peptidase. Refer to FIG. 4 for details relating to how these two peptidases work in degrading the MZ2-E antigen into its respective peptide fragments.

Thereafter, different peptide analogues of the synthetic peptide corresponding to the MZ2-E antigen, modified at one or both peptidase-sensitive position(s) were synthesized and their degradation properties tested. Refer to FIG. 3 and Table 1.

The data show that single-site protection (modification of one amino acid residue) at the amino-terminus of the peptide analogues was sufficient to protect the peptide bond locally at this terminus. Refer to FIG. 3, panel f. As well, single-site protection at the carboxy-terminus of the peptide analogues, exemplified in FIG. 3, panel k, was also sufficient to protect the peptide bond locally at the carboxy terminus. However, dual-site protected peptide analogues (modified at two amino acid residues, one at the amino terminus and the other at the carboxy terminus) were more stable than the single-site protected peptide analogues. Refer to FIG. 3, panel d.

That single- or dual-site protection increased half-life of the peptide analogues compared to the parent MZ2-E antigen becomes evident from Table 1. Therein, it is reported that the half-life of all the single-site and dual-site protected peptide analogues was substantially greater than that of the synthetic peptide corresponding to the MZ2-E antigen.

That all dual-site protected peptide analogues exhibited complete resistance to peptidase degradation as measured by a half-life of more than 8 hours is self evident from FIG. 3, panel d and Table 1.

As well, FIG. 3, shows that single-site protected peptide analogues did not fare as well compared to dual-site protected peptide analogues. For example, panels b-c show that single-site protected peptide analogues degraded faster than the dual-site protected peptide analogue exemplified in panel d.

Peptide fragments resulting from the actions of amino peptidases are shown in panels e and g. Peptide fragments resulting from the action of the dipeptidyl carboxy peptidases are shown in panels I-1. In addition, panel m shows a peptide fragment represented by the formula DPTGH, which results from the action of both the amino- and dipeptidyl carboxy peptidases.

Four (4) preferred dual-site protected peptide analogues contemplated by the invention are exemplified hereinafter:

[Aib$^2$, D-His$^7$]-MZ2-E

[D-Ala$^2$, D-Ser$^8$]-MZ2-E

[Aib$^2$, NMe-Ser$^8$]-MZ2-E

[NMe-Ala$^2$, NMe-Ser$^8$]-MZ2-E

The remainder of the peptides are exemplified in Table 1.

Aib refers to "-aminoisobutyric acid ("-methylalanine) while NMe-Ser refers to N-methyl-serine.

EXAMPLE III

HLA-A1 binding properties of MZ2-E and its analogues

Thereafter, studies relating to the affinity of the above structurally modified peptide analogs to bind to HLA-A1 was tested and compared to that of the parent peptide MZ2-E in a MHC stabilization assay. The BM36.1 cell line was used, which is deficient for the TAP function and expresses unstable MHC class I surface molecules (HLA-A1, B35 and Cw4). The unstable MHC molecules can be stabilized at the surface of such cell lines by peptides added exogenously in the culture medium. The stabilization of HLA-A1 on the surface of BM36.1 cells was detected by the monoclonal antibody W6.32, Yang et al., Immunogenetics, 19:217–231 (1984) and a fluorescent anti-mouse secondary antibody (Sigma) and analyzed by flow cytometry (Becton Dickinson FACScan). In the presence of increasing concentrations of peptide, a dose-effect curve was obtained allowing to define a SC50 value (stabilizing concentration 50: the concentration of peptide giving half of the maximal stabilization value) to be defined, reflecting the affinity of a given peptide for the MHC allele studied.

Referring to Table 1, right column, of the four preferred dual-site protected, fully resistant peptide analogues, one peptide analogue exemplified by [NMe-Ala$^2$, NMe-Ser$^8$]-MZ2-E exhibited a low affinity for HLA-A1, while another peptide analogue having the formula [D-Ala$^2$, D-Ser$^8$]-MZ2-E did not bind HLA-A1 at all.

In contrast, the structural modifications introduced in the sequence of the remaining two peptide analogues did not alter dramatically their affinity for MHC. Of these two peptide analogues, the peptide defined by the formula [Aib$^2$, NMe-Ser$^8$1-MZ2-E was favored over the peptide having the formula [Aib$^2$, D-His$^7$]-MZ2-E for its affinity for MHC.

MZ2-E-specific CTL activation

The preferred peptide analogues were also tested for their ability to sensitize target cells to lysis by a MZ2-E-specific CTL clone compared to the parent MZ2-E peptide.

Figure 5A:
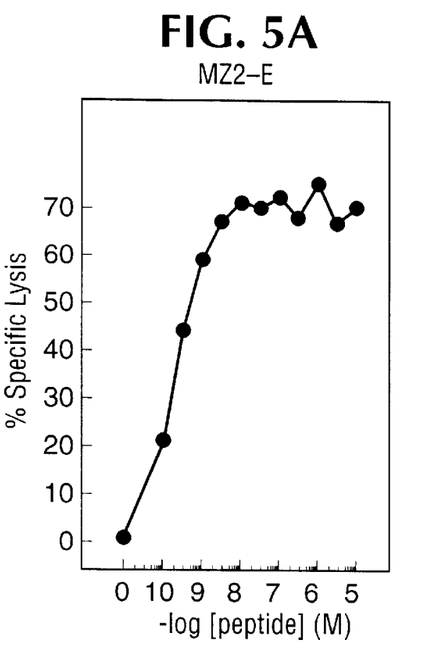
FIG. 5 collectively shows $^{51}$Cr release cell lysis studies using the BM 21 cell line. In particular, it shows recognition and lysis by MZ2-E specific CTL of target cells presenting MZ2-E or its analogues by measuring labeled Cr release.
Figure 5B:
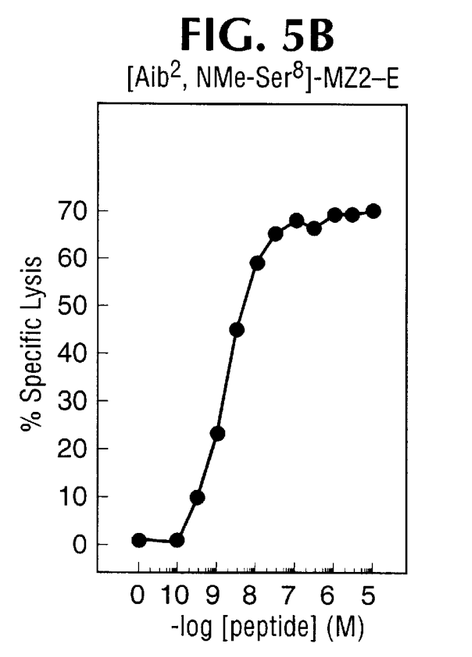
Figure 5C:
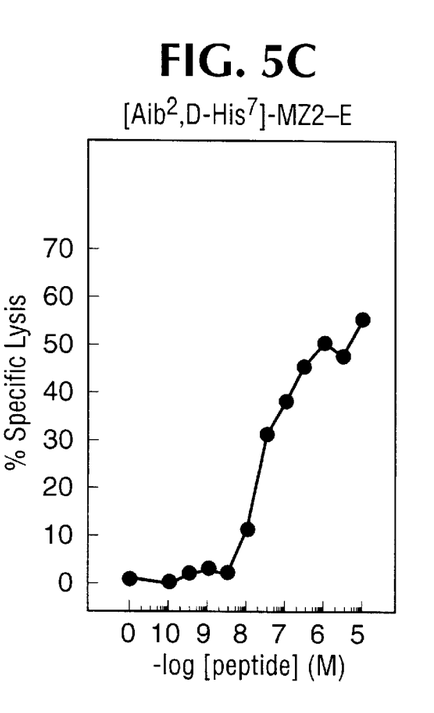
Figure 5D:
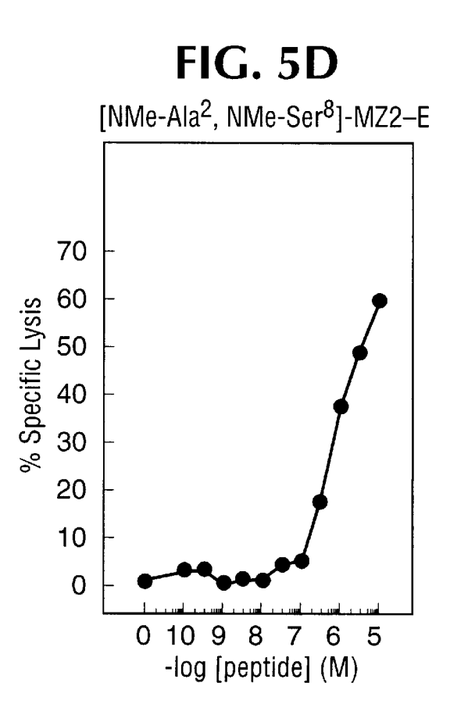

The lysis assay employed was a chromium release assay. Briefly, chromium-labeled HLA-A1 positive BM21 cells were incubated with increasing concentrations of the peptide analogues in the presence of monoclonal antibody W6.32. Anti-MZ2-E CTL clone 82/30, van der Bruggen et al., Science, 254:1643–1647 (1991), was then added as an effector cell and lysis of BM21 cells incubated with the different peptide analogues was observed and compared to that obtained with the parent synthetic peptide. The data are reported in FIG. 5 and summarized in Table 2. According to the data, the peptide analogue [Aib$^2$, NMe-Ser$^8$]-MZ2-E was able to sensitize the target cells (BM21) at concentrations comparable to that of the parent MZ2-E antigen. With respect to the remaining two peptide analogues exemplified in FIG. 5, it becomes apparent that increasing concentrations of the peptide analogue defined by the formula [NMe-Ala$^2$, NMe-Ser$^8$]-MZ2-E were needed to effectively lyse the cells, further corroborating the finding noted above, that this peptide analogue has a low affinity for HLA-A1.

The results in this experiment further corroborates the finding that the peptide analogue defined by the formula [Aib$^2$, NMe-Ser$^8$]-MZ2-E not only (1) resists complete peptidase degradation but also (2) sensitizes the target cells to lysis by the effector molecules at concentrations comparable to those of the parent MZ2-E antigen.

The foregoing examples show that the structurally modified peptide analogues of the MZ2-E antigen are presented by HLA-A1 molecules, and cells presenting the complex of HLA-A1 and the nonapeptide are recognized and lysed by specific CTL cells. This observation suggests that nonapeptides in accordance with the invention may be used both therapeutically and diagnostically.

Therapeutically, there are two major ways in which the nonapeptide may be used. In an in vivo therapeutic approach, the nonapeptides may be administered in a way which targets them to tumors to be treated. This can be done via direct injection, time release administration, coupling to tumor specific antibodies, and so forth. Upon binding the requisite HLA molecule, there is a CTL response, leading to lysis of the tumor. Of course, in such a therapeutic approach, the nonapeptide is administered in an amount sufficient to lead to lysis of the tumor. This amount will vary, based upon the particular patient, the type and size of the tumor, and so forth.

An "in vitro" form of therapy is also contemplated. As indicated supra, when the pertinent HLA molecule binds to the peptide analogue of the present invention, if contacted with the CTLs specific for the peptide analogue/HLA complex, a CTL proliferative response occurs. Since CTLs are the agents of tumor lysis in vivo, the resulting expanded populations may be administered to the patient. The CTLs can be expanded by using the patient's own blood or any other source of CTLs, or by contact to samples of peptide specific CTLs which have previously been established. In this regard, note that CTL 82/30, discussed supra has been available for some time as was the methodology for its development.

The peptide analogue may also be combined with one or more adjuvants which stimulate a more pronounced CTL response. Exemplary of such adjuvants are saponins and their analogues, such as those disclosed by U.S. Pat. No. 5,057,540 to Kensil et al., incorporated by reference or PCT application PCT/US92/03579 to Scott et al., also incorporated by reference. Of course, standard adjuvants, such as Freund's complete adjuvant, or Freund's incomplete adjuvant may also be used.

Therapies of the type described herein are particularly useful for melanoma. Analysis of samples has shown that about 40% of all melanoma tumors express MAGE-1, and the HLA-A1 allele is present in about 26% of the Caucasian population at large. Thus, at the least, 10% of the Caucasian melanoma population may be treated in this fashion.

These isolated peptide analogues when complexed to an HLA molecule, such as HLA-A1, may be combined with materials such as adjuvants to produce vaccines useful in treating pathological disorders characterized by presentation on surfaces of pathological cell of HLA/peptide complex of a type that differ from normal.

By "vaccine@s meant an agent such as the peptide analogues of the present invention which together with pharmaceutically acceptable adjuvants could be used to provoke an immune response when administered to a subject in need thereof. Administration of a vaccine contemplated by the invention to a patient may be by any known or standard method.

Further, the peptide analogues as well as complexes of the peptide analogues and HLA, may be used to produce antibodies, using standard techniques well known in the art.

To immunize the mice, a variety of different conventional protocols may be followed. For example, mice may receive primary and boosting immunizations of antigenic preparations containing the peptide analogues of the present invention.

Diagnostically, the peptides analogues may be used, for example, to identify tumors expressing a particular HLA molecule, or cancer cells per se. The method generally entails contacting a cancer cell containing sample or a tumor cell with a peptide analogue of the invention which binds thereto, and combines the material with a CTL sample specific for the complex. If lysis ensues, then the tumor/cancer cell can be typed with respect to the HLA molecule thus expressed.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

We claim:

1. An isolated peptide, consisting of from 8 to 11 amino acids, wherein said peptide:
   (a) binds to an HLA molecule,
   (b) has a half life greater than about 30 minutes relative to degradation by peptidase; and
   (c) wherein said peptide is modified with a group which inhibits degradation by peptidase at at least one of (i) an amino acid in the first two amino terminal residues or (ii) an amino acid in the last two carboxy terminal residues.

2. The isolated peptide according to claim 1 wherein said peptide binds to an HLA molecule on a cell surface to form a complex, and provokes lysis by cytolytic T cells specific for said complex.

3. The isolated peptide according to claim 1, wherein said peptide consists of 9 amino acids, wherein amino acid residue 2 is selected from the group consisting of Val, Ala, D-Ala, NMe-Ala, Aib, and amino residue 9 is selected from the group consisting of tyrosine and tyrosine-amide.

4. The isolated peptide according to claim 3, wherein amino acid residue 8 is NMe-Ser.

5. The isolated peptide according to claim 3, wherein amino acid residue 2 is selected from the group consisting of Val and Ala, and said amino residue 9 is Tyrosine.

6. The isolated peptide according to claim 3, wherein amino acid residue 1 is D-Glu.

7. The isolated peptide according to claim 3, wherein amino acid residue 1 is NMe-Glu.

8. The isolated peptide according to claim 3, wherein amino acid residue 2 is D-Ala.

9. The isolated peptide according to claim 3, wherein amino acid residue 2 is NMe-Ala.

10. The isolated peptide according to claim 3, wherein amino acid residue 2 is Aib.

11. The isolated peptide according to claim 3, wherein amino acid residue 7 is D-His.

12. The isolated peptide according to claim 3, wherein amino acid residue 8 is D-Ser.

13. The isolated peptide according to claim 3, wherein amino acid residue 8 is NMe-Ser.

14. The isolated peptide according to claim 3, wherein said amino acid residue 9 is Tyr-amide.

15. The isolated peptide according to claim 3, wherein said amino acid residue 2 is Aib and amino acid residue 7 is D-His.

16. The isolated peptide according to claim 3, wherein said amino acid residue 2 is D-Ala and amino acid residue 8 is D-Ser.

17. The isolated peptide according to claim 3, wherein said amino acid residue 2 is Aib and amino acid residue 8 is NMe-Ser.

18. The isolated peptide according to claim 3, wherein said amino acid residue 2 is NMe-Ala and amino acid residue 8 is NMe-Ser.

19. The isolated peptide according to claim 3, wherein said amino acid residue 2 is Aib and said amino acid residue 9 is Tyr-amide.

20. The isolated peptide of claim 1, selected from the group consisting of:
   (a) Glu-Aib-Asp-Pro-Thr-Gly-His-NMe-Ser-Tyr,
   (b) Glu-D-Ala-Asp-Pro-Thr-Gly-His-D-Ser-Tyr,
   (c) Glu-NMe-Ala-Asp-Pro-Thr-Gly-His-NMe-Ser-Tyr, and
   (d) Glu-D-Ala-Asp-Pro-Thr-Gly-His-D-Ser-Tyr.

21. The isolated peptide according to claim 19, wherein said peptide is defined by the amino acid sequence:

Glu-Aib-Asp-Pro-Thr-Gly-His-NMe-Ser-Tyr.

22. Method of producing the peptide according to claim 1 comprising:
   (a) producing a synthetic peptide using linear synthesis, and
   (b) modifying said synthetic peptide to resist peptidase degradation.

23. An immunogenic composition comprising the peptide of claim 1, and a pharmaceutically acceptable adjuvant.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 9 amino acids
      (B) TYPE: amino acid
      (C) STRANDEDNESS: single
      (D) TOPOLOGY: linear    (ii) MOLECULE TYPE:    protein    (xi) SEQUENCE DESCRIPTION:  SEQ ID NO: 1:

Glu Ala Asp Pro Thr Gly His Ser Tyr
1           5

(2) INFORMATION FOR SEQ ID NO: 2:

(i) SEQUENCE CHARACTERISTICS:
      (A) LENGTH: 9 amino acids
      (B) TYPE: amino acid
      (C) STRANDEDNESS: single
      (D) TOPOLOGY: linear    (ii) MOLECULE TYPE:    protein    (xi) FEATURE:
      (D) OTHER INFORMATION: Xaa is D-Glu    (xi) SEQUENCE DESCRIPTION:  SEQ ID NO: 2:

Xaa Ala Asp Pro Thr Gly His Ser Tyr
1           5

(2) INFORMATION FOR SEQ ID NO: 3:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE:      protein (xi) FEATURE:
             (D) OTHER INFORMATION: Xaa is NMe-GLu (xi) SEQUENCE DESCRIPTION:   SEQ ID NO: 3:

Xaa Ala Asp Pro Thr Gly His Ser Tyr
1               5

(2) INFORMATION FOR SEQ ID NO: 4:

(i) SEQUENCE CHARACTERISTICS:
             (A) LENGTH: 9 amino
             (B) TYPE: amino acid
             (C) STRANDEDNESS: single
             (D) TOPOLOGY: linear (ii) MOLECULE TYPE:      protein (xi) FEATURE:
             (D) OTHER INFORMATION: Xaa is D-Ala (xi) SEQUENCE DESCRIPTION:   SEQ ID NO: 4:

Glu Xaa Asp Pro Thr Gly His Ser Tyr
1               5

(2) INFORMATION FOR SEQ ID NO: 5:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE:      protein (xi) FEATURE:
             (D) OTHER INFORMATION: Xaa is NMe-Ala (xi) SEQUENCE DESCRIPTION:   SEQ ID NO: 5:

Glu Xaa Asp Pro Thr Gly His Ser Tyr
1               5

(2) INFORMATION FOR SEQ ID NO: 6:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE:      protein (xi) FEATURE:
             (D) OTHER INFORMATION: Xaa is Aib (xi) SEQUENCE DESCRIPTION:   SEQ ID NO: 6:

Glu Xaa Asp Pro Thr Gly His Ser Tyr
1               5

(2) INFORMATION FOR SEQ ID NO: 7:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE:      protein

```
    (xi) FEATURE:
         (D) OTHER INFORMATION: Xaa is D-His (xi) SEQUENCE DESCRIPTION:     SEQ ID NO: 7:

Glu Ala Asp Pro Thr Gly Xaa Ser Tyr
1               5

(2) INFORMATION FOR SEQ ID NO: 8:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE:     protein (xi) FEATURE:
         (D) OTHER INFORMATION: Xaa is D-Ser (xi) SEQUENCE DESCRIPTION:     SEQ ID NO: 8:

Glu Ala Asp Pro Thr Gly His Xaa Tyr
1               5

(2) INFORMATION FOR SEQ ID NO: 9:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE:     protein (xi) FEATURE:
         (D) OTHER INFORMATION: Xaa is NMe-Ser (xi) SEQUENCE DESCRIPTION:     SEQ ID NO: 9:

Glu Ala Asp Pro Thr Gly His Xaa Tyr
1               5

(2) INFORMATION FOR SEQ ID NO: 10:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE:     protein (xi) FEATURE:
         (D) OTHER INFORMATION: Xaa is Tyr-amide (xi) SEQUENCE DESCRIPTION:     SEQ ID NO: 10:

Glu Ala Asp Pro Thr Gly His Ser Xaa
1               5

(2) INFORMATION FOR SEQ ID NO: 11:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE:     protein (xi) FEATURE:
         (D) OTHER INFORMATION: The first Xaa is alpha-methylalanine
              and the second Xaa is D-His
```

(xi) SEQUENCE DESCRIPTION: SEQ ID NO: 11:

Glu Xaa Asp Pro Thr Gly Xaa Ser Tyr
1               5

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE:    protein (xi) FEATURE:
        (D) OTHER INFORMATION: The first Xaa is D-Ala.
            D-Ser (xi) SEQUENCE DESCRIPTION: SEQ ID NO: 12:

Glu Xaa Asp Pro Thr Gly His Xaa Tyr
1               5

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE:    protein (xi) FEATURE:
        (D) OTHER INFORMATION: The fist Xaa is alpha-methylalanine
            and the second Xaa is NMe-Ser (xi) SEQUENCE DESCRIPTION: SEQ ID NO: 13:

Glu Xaa Asp Pro Thr Gly His Xaa Tyr
1               5

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE:    protein (xi) FEATURE:
        (D) OTHER INFORMATION: The first Xaa is NMe-Ala
            Xaa is NMe-Ser (xi) SEQUENCE DESCRIPTION: SEQ ID NO: 14:

Glu Xaa Asp Pro Thr Gly His Xaa Tyr
1               5

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE:    protein (xi) FEATURE:
        (D) OTHER INFORMATION: The first Xaa is alpha-methylalanine
            and the second Xaa is Tyr-amide (xi) SEQUENCE DESCRIPTION: SEQ ID NO: 15:

Glu Xaa Asp Pro Thr Gly His Ser Xaa
1               5